US012465508B2

(12) United States Patent
Dholakia et al.

(10) Patent No.: US 12,465,508 B2
(45) **Date of Patent: *Nov. 11, 2025**

(54) STENT AND STENT DELIVERY

(71) Applicant: MicroVention, Inc., Aliso Viejo, CA (US)

(72) Inventors: Ronak Dholakia, Los Angeles, CA (US); Hussain S. Rangwala, Villa Park, CA (US); William R. Patterson, Huntington Beach, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 100 days.

This patent is subject to a terminal disclaimer.

(21) Appl. No.: 18/201,004

(22) Filed: May 23, 2023

(65) Prior Publication Data

US 2024/0325176 A1 Oct. 3, 2024

Related U.S. Application Data

(63) Continuation of application No. 16/818,782, filed on Mar. 13, 2020, now Pat. No. 11,690,740.

(60) Provisional application No. 62/817,988, filed on Mar. 13, 2019.

(51) Int. Cl.

*A61F 2/88* (2006.01)
*A61F 2/966* (2013.01)
*A61F 2/97* (2013.01)
*A61F 2/82* (2013.01)

(52) U.S. Cl.

CPC ................ *A61F 2/88* (2013.01); *A61F 2/966* (2013.01); *A61F 2/97* (2013.01); *A61F 2002/823* (2013.01); *A61F 2250/0023* (2013.01)

(58) Field of Classification Search

CPC .. A61F 2/95; A61F 2/966; A61F 2/962; A61F 2/9661; A61F 2/9662; A61F 2/954; A61F 2/9522; A61F 2/97; A61F 2/88; A61F 2/86; A61F 2/90; A61F 2/0095; A61F 2002/9505; A61F 2002/9511;
(Continued)

(56) References Cited

U.S. PATENT DOCUMENTS 5,201,757 A * 4/1993 Heyn ........................ A61F 2/95 606/198
6,428,566 B1 * 8/2002 Holt ........................ A61F 2/966 604/525
9,301,831 B2 4/2016 Kusleika et al.
(Continued)

FOREIGN PATENT DOCUMENTS

WO 2020/186210 A1 9/2020

OTHER PUBLICATIONS

International Search Report and Written Opinion, mailed Jun. 9, 2020, for International Application No. PCT/US2020/022745 filed on Mar. 13, 2020.

*Primary Examiner* — Diane D Yabut
(74) *Attorney, Agent, or Firm* — K&L Gates LLP; Brian Novak; Giorgios N. Kefallinos

(57) ABSTRACT

A vascular prosthesis (e.g., stent), and packaging and delivery system to selectively deliver a vascular prosthesis are described. In some embodiments, the vascular prosthesis utilizes a low porosity and high porosity section, and the packaging and delivery system allows the prosthesis to be delivered such that the position of the low porosity and high porosity sections of the prosthesis can vary.

20 Claims, 11 Drawing Sheets

(58) Field of Classification Search
CPC ........ A61F 2002/9665; A61F 2002/823; A61F 2250/0023
See application file for complete search history.

(56) References Cited

U.S. PATENT DOCUMENTS

| | | | |
|---|---|---|---|
| 9,439,791 B2 | 9/2016 | Vong et al. | |
| 9,474,639 B2 | 10/2016 | Haggstrom et al. | |
| 10,004,618 B2 | 6/2018 | Berez et al. | |
| 11,690,740 B2 * | 7/2023 | Dholakia .................. | A61F 2/97 623/1.12 |
| 2010/0049297 A1 | 2/2010 | Dorn | |
| 2012/0181193 A1 | 7/2012 | Wu | |
| 2012/0259404 A1 | 10/2012 | Tieu et al. | |
| 2013/0245745 A1 | 9/2013 | Vong et al. | |
| 2014/0121745 A1 | 5/2014 | Kusleika et al. | |
| 2016/0206452 A1 | 7/2016 | Berez et al. | |
| 2017/0079819 A1 | 3/2017 | Pung et al. | |

* cited by examiner

STENT AND STENT DELIVERY

RELATED APPLICATIONS

This application is a continuation of U.S. Ser. No. 16/818,782, filed Mar. 13, 2020, which claims priority to U.S. Provisional Application Ser. No. 62/817,988, filed Mar. 13, 2019, entitled Stent and Stent Delivery, each of which is incorporated herein by reference in its entirety.

BACKGROUND

Vascular prosthesis such as stents are used for a variety of reasons in the vasculature, including but not limited to, propping open blood vessels to restore patency or treating sclerotic buildup, delivering drugs, acting as a scaffold to retain embolic material, and diverting blood flow from a region of interest such as an aneurysm—this last class of stents are known as flow diverters. The flow diverter is placed in the vessel adjacent to the aneurysm and across the neck of the aneurysm to reduce blood flow into the aneurysm, thereby reducing the risk of aneurysm rupture. Over time, endothelial growth will take place over and around the stent, closing off the aneurysm and restoring normal blood flow in the target area.

One issue with using these flow-diversion stents is the difficulty in having one stent that treats a complete vascular region effectively. Typical flow diversion stents utilize a constant, low-porosity profile along the entire length of the stent. This can be problematic where only a portion of the stent is useful for flow diversion purposes. For example, part of the stent may sit adjacent an aneurysm region where low porosity/large resistance to blood flow is beneficial to limit blood flow into the aneurysm. However, another section of the stent may overlie a nearby branch artery, where low porosity would limit blood flow into the branch artery, thereby negatively effecting the natural flow of blood. A typical flow diversion stent would have a consistent porosity profile, reducing blood flow into the branch artery as well as the aneurysm location. The reduction of blood flow into the normal branch artery can cause complications over time due to reduced oxygenation within this arterial region. Therefore, while the flow diversion interface can effectively treat the aneurysm, it can cause complications in an adjoining region that does not require flow diversion.

There is a need for a stent/stent delivery platform that has the ability to treat a variety of regions and conditions and address these issues.

SUMMARY

Vascular prosthesis devices, packaging or packing for these devices, and methods of using these devices are described. In one embodiment, the vascular prosthesis device is a stent. In one embodiment, the stent is composed of multiple layers (e.g. two or more layers). In one embodiment, the stent has two layers. In one embodiment, the stent has a variable porosity profile along longitudinal sections of the stent, where part of the stent has a first porosity profile and another part of the stent has a second porosity profile. In one embodiment, a stent is comprised of metallic braided wires. In one embodiment, a dual-layer braided stent with a variable longitudinal profile is described. In one embodiment, one longitudinal portion of a stent utilizes a first porosity while another longitudinal portion of the stent utilizes a different, second porosity. In one embodiment, the stent is configured as a flow diversion stent to divert blood flow from an aneurysm, where the stent has a first section with a porosity profile that functions as a flow diverter and a second section with a higher porosity profile that does not function as a follow diverter.

In one embodiment, the vascular prosthesis device can either be delivered in a first or second configuration to customize which portion of the stent utilizes a low porosity, flow diversion portion. In a first configuration, a low porosity flow diversion layer is on one portion (e.g., a proximal portion) of the stent and a high porosity layer is on another portion (e.g., a distal section) of the stent. In a second configuration, a low porosity flow diversion layer is on one portion (e.g., a distal portion) of the stent and a high porosity layer is on another portion (e.g., a proximal portion) of the stent. The stent can be selectively delivered either in the first configuration where flow diversion is useful on a particular section (e.g., a proximal portion) of the stent, or in the second configuration where flow diversion is useful on another particular section (e.g., a distal section) of the stent.

A vascular prosthesis (e.g., stent) system is described. In one embodiment, the system includes packaging utilizing a housing containing a stent and at least a first tubing connected to a first end of the packaging or housing and at least a second tubing connected to a second end of the housing. Each of the first tubing and the second tubing contains an introducer sleeve used to selectively introduce the stent into a delivery catheter. The stent utilizes a variable porosity profile where a certain length of the stent utilizes a first porosity and another length of the stent utilizes a different, second porosity. When the stent is advanced along a first direction through a first tube, the porosity profile is such that a lower porosity interface (e.g., configured for flow diversion) is on one portion of the stent (e.g., a proximal portion) and a higher porosity interface is on another portion (e.g., a distal portion) of the stent. When the stent is advanced along a second direction through a second tube, the porosity profile is switched such that the lower porosity interface useful for flow-diversion is on one portion of the stent (e.g., a distal portion) and a higher porosity interface is on another portion (e.g., a proximal portion) of the stent. In this way, a user can customize which section of the stent is used for flow diversion by pushing the stent through either a first introducer tube or a second introducer tube.

In one embodiment, a vascular prosthesis system utilizes a mechanical pushing system. In one embodiment, the vascular prosthesis system utilizes a mechanical delivery pusher connected to each end of the stent used to deliver the stent through a tubing region-such that a first pusher engages a first part of the stent and a second pusher engages a second part of the stent. When the stent is propelled in a first direction through the first tube, the pusher on the one side of the stent stays engaged with the stent to direct it through that first tube, while the pusher on the other side of the stent disengages. When the stent is propelled in a second direction through the second tube, the pusher on the one side of the stent stays engaged with the stent to direct it through that second tube, while the stent on the other side of the stent disengages.

In one embodiment, a method of delivering a vascular prosthesis device (e.g., a stent) is described. The stent has a variable porosity profile, where a portion of the stent utilizes a low porosity interface (e.g., configured for flow diversion). The stent is contained in a housing with tubing on either side of the housing, and a mechanical pusher element on either end of the stent. The stent is selectively pushed in a first direction to direct the stent through a first tubing—in this way the flow diversion layer is on a particular portion (e.g., a proximal portion) of the stent. Alternatively, the stent is selectively pushed in a second direction to direct the stent through a second tubing—and in this way the flow diversion layer is on another portion (e.g., a distal portion) of the stent. Each tubing contains an introducer sleeve, which the stent is introduced into when the stent is delivered from the housing and into the tubing. The stent and overlying introducer sleeve are delivered out of the tubing. The introducer sleeve is then placed near a proximal end of the catheter, and the stent is advanced into and through the catheter to the treatment site in a patient vasculature.

In one embodiment, a method of treating a patient with a prosthesis device (e.g., a stent) is described. The stent utilizes a variable porosity interface, with a low porosity layer on a particular portion of the stent. In one embodiment, this low porosity layer is configured for flow diversion. The stent is contained in a housing and conveyed by a user into an introducer sleeve and through a particular tubing section in order to get low porosity flow diversion layer on either a proximal or distal section of the stent, depending on the condition of the vasculature and where flow diversion is needed. The introducer sleeve (containing an indwelling stent) are placed near a proximal end of the catheter, and the stent is advanced through the introducer sleeve and into and through the catheter to the treatment site in a patient vasculature.

In some embodiments, vascular prosthesis systems are described including a vascular prosthesis having a lower porosity region and a higher porosity region; a housing containing the vascular prosthesis; ad a first tubing linked to a first end of the housing, a second tubing linked to a second end of the housing, wherein the vascular prosthesis is deliverable through the first tubing or the second tubing.

In some embodiments, the first tubing and second tubing each include an introducer sleeve. The first tubing and second tubing can both be coiled. In other embodiments, terminal ends of the vascular prosthesis are pre-loaded into each introducer sleeve. The introducer sleeve can span a portion of the housing.

In some embodiments, the systems can further include a pin which engages the introducer sleeve.

In some embodiments, delivery through the first tubing causes the lower porosity region to be on a proximal region of the vascular prosthesis, and delivery through the second tubing causes the lower porosity region to be on a distal region of the vascular prosthesis.

Also described herein are vascular prosthesis systems including a vascular prosthesis having a first porosity region and a second porosity region; a housing containing the vascular prosthesis; and a first tubing linked to a first end of the housing, a second tubing linked to a second end of the housing; the vascular prosthesis being deliverable through the first tubing or the second tubing. In some embodiments, if the vascular prosthesis is delivered through the first tubing, then the first porosity region is on a first longitudinal section of the vascular prosthesis; and if the vascular prosthesis is delivered through the second tubing, then the first porosity is on a second longitudinal section of the vascular prosthesis.

In other embodiments, the systems further comprise a first pusher connected to a first section of the vascular prosthesis, and a second pusher connected to a second section of the vascular prosthesis. The first pusher can be used to navigate the vascular prosthesis through the first tubing and the second pusher is used to navigate the vascular prosthesis through the second tubing. The first pusher can disengage from the first section of the vascular prosthesis. The second pusher can disengage from the second section of the vascular prosthesis. The vascular prosthesis can include flared ends, wherein the first and second pusher engage the flared ends of the vascular prosthesis. In some embodiments, the first pusher disengages from the vascular prosthesis as the vascular prosthesis is delivered through the second tubing. In other embodiments, the second pusher disengages from the vascular prosthesis as the vascular prosthesis is delivered through the first tubing.

Also described herein are flow diverting prosthesis systems including a vascular prothesis having a flow diversion region with a lower porosity and a non-flow diversion region with a higher porosity; a housing containing the vascular prosthesis; and a first tubing linked to a first end of the housing, a second tubing linked to a second end of the housing; the vascular prosthesis being deliverable through the first tubing or the second tubing. In some embodiments, if the vascular prosthesis is delivered through the first tubing, then the flow diversion region is on a first longitudinal section of the vascular prosthesis; and if the vascular prosthesis is delivered through the second tubing, then the flow diversion region is on a second longitudinal section of the vascular prosthesis.

In some embodiments, the housing has a first housing section, second housing section, and a gap in between. In other embodiments, a lumen of the housing is larger than a lumen of the first tubing and a lumen of the second tubing. In other embodiments, an outer diameter of the housing is larger than an outer diameter of the first tubing and an outer diameter of the second tubing.

Delivery through the first tubing can cause the flow diversion region to be on a proximal region of the vascular prosthesis, and delivery through the second tubing can cause the flow diversion region to be on a distal region of the vascular prosthesis.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Vascular prostheses such as stents can be used for a variety of reasons and to treat a variety of conditions, as described above. Flow diversion stents are one particular class of vascular prostheses which utilize a relatively low porosity interface in order to divert flow away from a particular vascular region. Flow diversion stents are one potential treatment option for aneurysms. The flow diversion stent is placed against the neck or opening of the aneurysm, where the low porosity interface limits blood flow into the aneurysm, reducing the risk of rupture. Over time, endothelial tissue grows over the stent to cut off blood flow into the aneurysm.

U.S. Pat. Nos. 9,867,725 and 9,439,791 disclose information about stents, dual-layer stents, and flow diversion stents and are both hereby incorporated by reference in their entirety.

Figure 1:
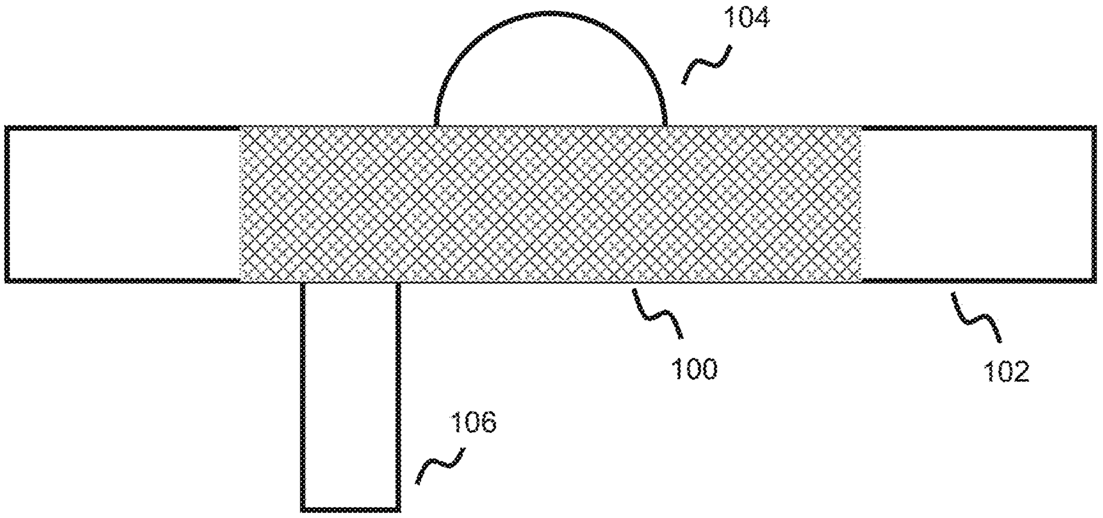
FIG. 1 illustrates a typical flow diversion stent being used to treat an aneurysm.

Though flow diversion stenting is an effective way to treat aneurysms, there are potential complications with the procedure. Flow diverting stents utilize a consistent porosity across the entire length of the stent. This can cause issues where an aneurysm is located in close proximity to a branched blood vessel and the flow diverting stent will overlie both the aneurysm and the nearby branched blood vessel. The flow diversion interface is useful for the section adjacent to the aneurysm, but is not useful for the section of the stent adjacent to the branched blood vessel since reduced blood flow to the blood vessel can negatively impact normal blood circulation through the body-potentially introducing additional complications. This scenario is shown in FIG. 1, where a flow diverting stent 100 is used to treat a sidewall aneurysm 104 along a blood vessel 102, but also overlies a nearby branched vessel 106 thereby affecting blood flow through the branched vessel.

Figure 2:
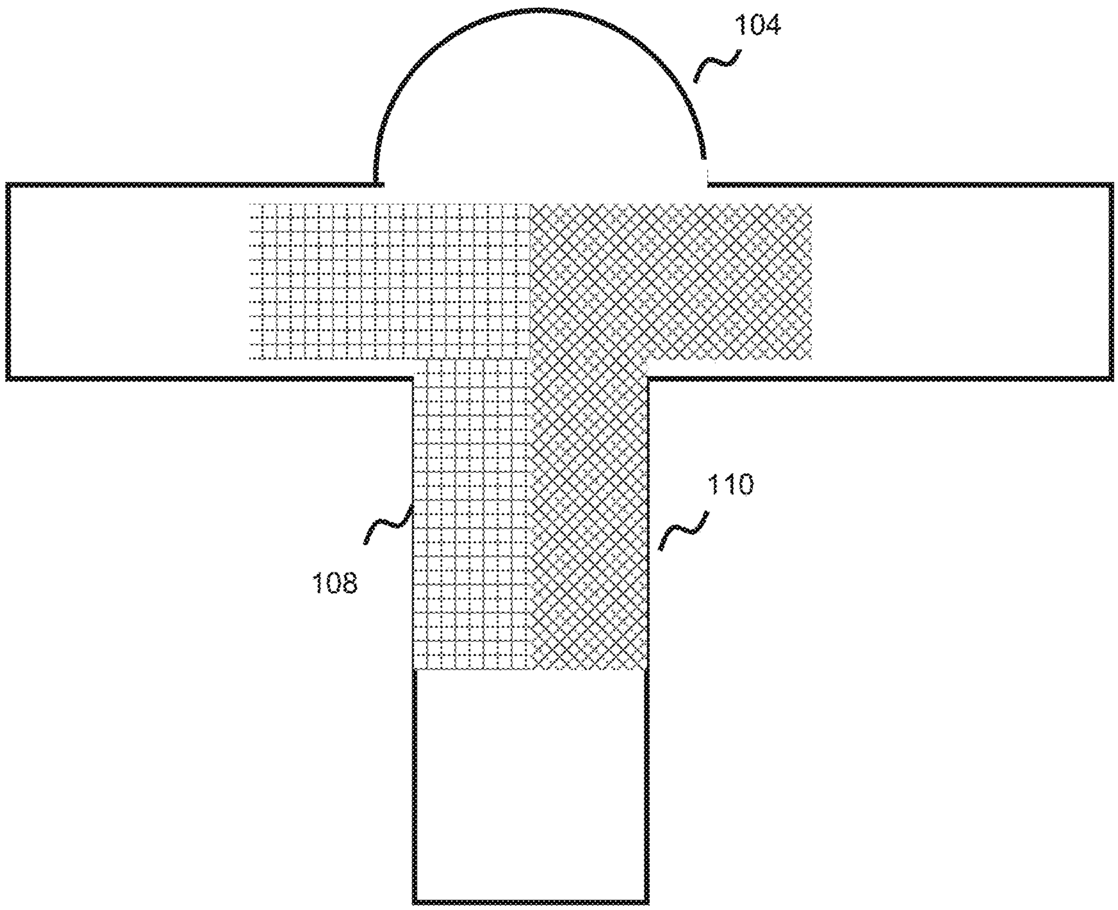
FIG. 2 illustrates a stenting technique used to treat a bifurcation aneurysm utilizing two flow diversion stents.

Flow diversion stents can also be used to treat bifurcation aneurysms. Aneurysms can commonly be located along blood vessel bifurcations since there is a great deal of blood pressure exerted on the vessel wall at a vessel bifurcation junction. Since multiple blood vessels are present at these junctions, two stents are placed across the aneurysm, often one low porosity flow diversion stent is placed through another high porosity stent (commonly called Y-stenting since a Y-shape is created). Another technique, shown in FIG. 2, is known as a kissing technique where two low porosity stents can be placed next to each other, to reduce blood flow into the aneurysm. Since the flow diversion stents utilize a consistent low porosity profile and only a portion of the stent is needed for flow diversion purposes, the stent may negatively affect blood flow through this region. This could happen, for instance, if the stent is not aligned flush against the vessel wall and the large amount of metal surface coverage used to create the low porosity profile impedes blood flow. This can also happen in the scenario shown in FIG. 2 where the stents are laid against each other across the blood vessel, thereby creating an obstacle to blood flow.

Figure 3:
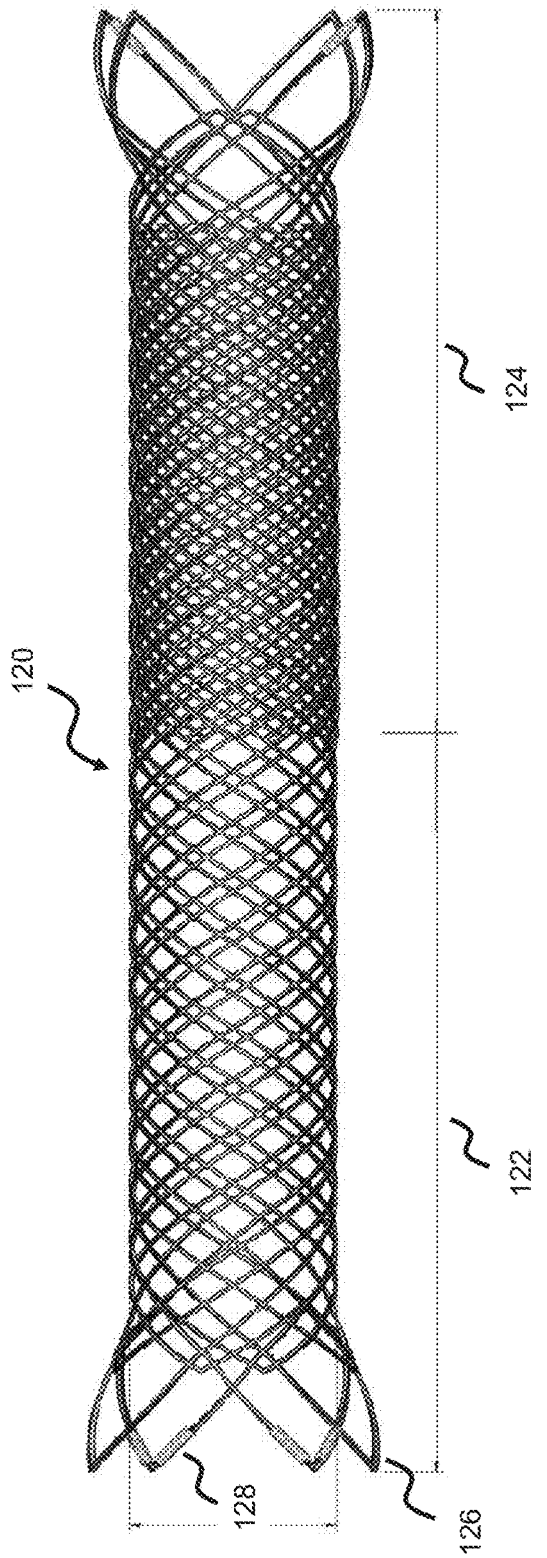
FIG. 3 illustrates a variable porosity flow diversion stent, according to one embodiment.

One solution to these issues is to have a stent with a variable profile, as shown in FIG. 3—where only a portion of the stent utilizes a flow diversion interface. In one embodiment, the stent is a mesh of braided metallic wires. Preferably a strong-shape memory material such as nitinol, stainless steel, colbalt-chromium, or drawn filled tubing (e.g. platinum core with a nitinol jacket) wires are used. Stent 120 utilizes a first region 122 with a high porosity, this section has relatively low metal surface coverage as indicated in FIG. 3—meaning the pores formed by various wire crossings are larger compared to a lower porosity region of the stent. Stent 120 also utilizes a second region 124 with a low porosity, this section has a relatively high metal surface coverage—meaning the pores formed by the various wire crossing points are smaller compared to the higher porosity region of the stent.

The low porosity region, such as second region 124, can be configured in various ways. In one embodiment, the entire stent comprises a common, high porosity layer sitting along an entire longitudinal length of the stent, and the lower porosity region of the stent is composed of an additional low porosity layer either above or below this common, high porosity layer—where the lower porosity region of the stent utilizes a layer with a denser or less "open" braiding pattern; in this way there is a defined high porosity section, such as first region 122, (composed solely of the more porously wounded wire section/layer) and low porosity section, such as second region 124, (composed both of a more porous layer with a more dense layer located directly above or below this layer). In one embodiment, the low porosity layer or section is located radially within the high porosity layer along the low porosity portion of the stent. In one embodiment, the low porosity layer is located radially outward of the high porosity layer along the portion of the stent utilizing the low porosity interface. In this way, a portion of the stent has a higher porosity and another portion of the stent has a lower porosity. This lower porosity section of the stent is considered the flow-diversion portion of the stent, and in practice this is the region of the stent that would be placed along the neck of the aneurysm and thereby used to treat the aneurysm.

By way of example, where a first layer runs the length of the device and is construed as an outer layer, and an inner/second layer acts as flow diversion portion and sits radially within a longitudinal portion of the outer layer, the outer layer wire diameter can range between 0.002"-0.003" and the inner layer wire diameter can range from 0.00075"-0.001". The outer layer can have 1-36, 6-24, or 12-18 wires and the inner layer can have between 36-64 wires depending on the device size.

In other embodiments, a first layer runs the length of the device and is construed as an inner layer, and an outer/second layer acts as a flow diversion portion and sits radially outside a portion of the inner layer.

In one embodiment, a first high porosity metallic section which defines an entire length of the stent is composed of solely one wire which is wound back and forth over a mandrel to define a generally tubular shape. The low porosity section is then formed of a plurality of metallic wires (e.g. 12-24 or more) separately wound/braided and then placed below the high porosity section along a particular portion of the stent, to define a distinct high porosity section and a defined low porosity section.

In alternate embodiments, the stent is composed of just one braided layer. However, the lower porosity portion of the stent utilizes a tighter or more dense winding pattern to create a flow diversion portion. In one example, the stent is wound over a common mandrel, but the lower porosity flow diversion portion of the stent utilizes a denser winding pattern along that particular mandrel section to create a denser braid profile.

In other embodiments, the stent is not composed of braided wires. Instead, a laser cut metallic or polymeric sheet is used where a higher porosity portion of the stent utilizes a more open profile (meaning more cuts or openings are used along this section) while a lower porosity portion of the stent utilizes a less open profile (meaning less cuts or openings are used along this section).

In one embodiment, the stent includes a plurality of outwardly projecting flares 126 at either end of the stent, for instance 2-10 flares. The flares help to stabilize the stent in the vessel and, as will be explained later, can provide a mechanism to connect the stent to a pusher element, which helps navigate and deliver the stent. Flares 126 can further include radiopaque marker bands or coils 128 wrapped around portions of the flare. Coils 128 help visualize the ends of the stent during the stent delivery process and, as will be explained later, can further enable connection to the delivery pusher. In one embodiment, all flares 126 are of a similar size. In one embodiment, the flares 126 are of different sizes such that some flares are larger and some flares are smaller. In one embodiment, flares 126 are arranged in an alternating manner such that one larger flare sits next to a smaller flare, where this pattern continues around the periphery of the end of the stent.

Figure 4:
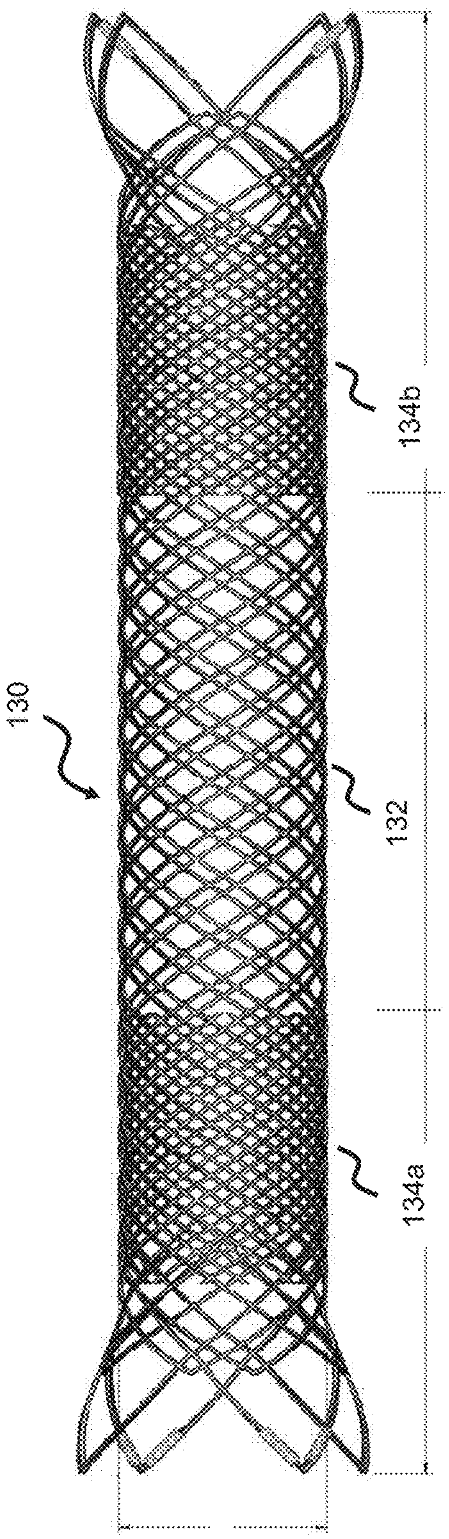
FIG. 4 illustrates a variable porosity flow diversion stent, according to another embodiment.

Although the stent as FIG. 3 shows just two interface segments—a first high porosity portion, first region 122, and a low porosity portion, second region 124, next to the high porosity portion, various interfaces are possible in different embodiments. For instance, a stent with 3 longitudinal portions—a middle low porosity portion and two high porosity portions on either side; or alternatively—as shown in FIG. 4—a middle high porosity portion 132 and two low porosity portions 134*a*, 134*b* on either side.

Alternatively, more than three segments can be used utilizing various combinations of high porosity and low porosity portions. Furthermore, where plural high porosity and plural low porosity sections are used, each section can utilize a distinct porosity profile—meaning the plural high porosity sections can each utilize different high porosity interfaces (e.g., different braiding profiles resulting in different pore sizes) while the plural low porosity sections can each utilize distinct low porosity interfaces.

Alternatively still, a low porosity and/or high porosity region can utilize a variable porosity within that porosity region. For example, a low porosity region can have a variable porosity configuration such that the pore sizes change over the length of the low porosity region within a particular low-porosity range. Similarly, a high porosity region can have a variable porosity configuration such that the pore sizes change over the length of the high porosity region within a particular high-porosity range.

Figure 5:
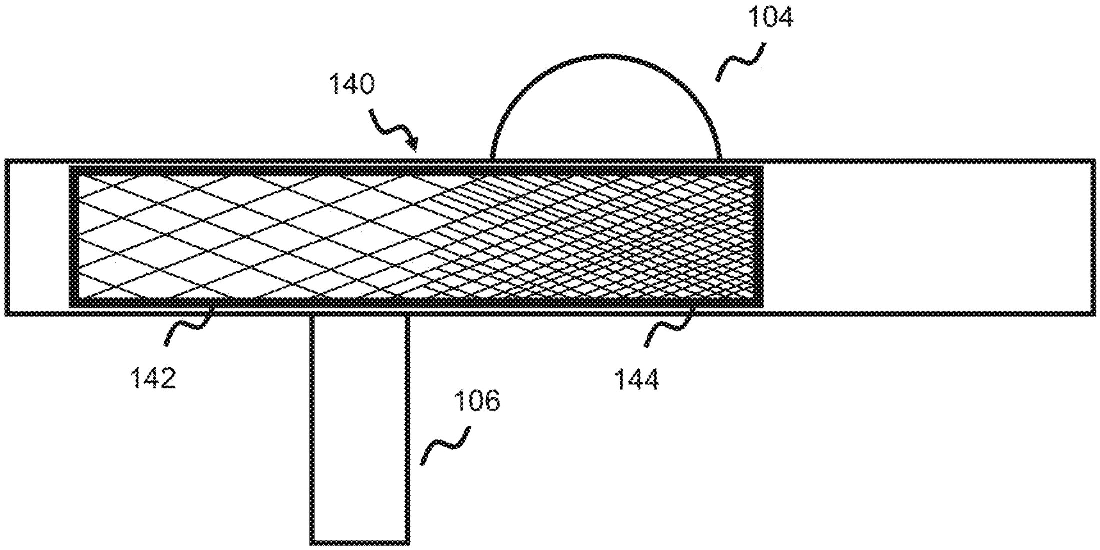
FIG. 5 illustrates a variable porosity flow diversion stent used to treat an aneurysm, according to one embodiment.

As shown in FIG. 5, with a variable porosity stent design utilizing a low porosity/flow diversion portion 144 and a high porosity portion 142, the lower porosity region of the stent can be placed against the aneurysm neck to treat the aneurysm 104. However, the rest of the stent will utilize a high porosity interface, so blood flow to any branched vessels near the stent will not necessarily suffer since the branched vessel region is overlaid by a high porosity interface, representing less of a barrier to blood flow than the low porosity interface.

Flow diverting stents often utilize a percentage to define the level of flow diversion. This percentage can be reflected in one of two ways. The first percentage calculation refers to material surface coverage that is the percent of the overall area of the stent that comprises actual material. In the context of a braided metallic stent, this would refer to the portion of the complete stent area that comprises metallic wire. This calculation would reflect the ratio of the total surface area of the wires comprising the stent (meaning the total surface area the wires occupy) to the total surface area of the stent. The second percentage calculation is a porosity percentage and reflects the amount of open space that does not include metallic wire. This can be thought of as the proportion of the stent that is just pores. In other words, the ratio of the open space or pores of the stent to the total surface area of the stent. The porosity percentage plus the material surface coverage adds up to 100%, and in this way, these two percentages are related.

In some embodiments, a stent can be classified as a flow diverter if the porosity percentage is between about 50 and about 75 percent. In this way, where a variable porosity stent as described herein can utilize a section meant for flow diversion, the porosity percentage of that particular section can be between about 50 and about 75 percent while the section of the stent not meant for flow diversion has a higher porosity percentage. In some embodiments, that higher porosity can have a porosity percentage of between about 80 and about 95 percent.

In other embodiments, a variable porosity stent can include a section meant for flow diversion having a porosity percentage of between about 40 and about 80 percent, about 30 and about 80 percent, about 20 and about 80 percent, about 10 and about 80 percent, about 40 and about 70 percent, about 30 and about 70 percent, about 20 and about 70 percent, about 10 and about 70 percent, about 40 and about 60 percent, about 30 and about 60 percent, about 20 and about 60 percent, about 10 and about 60 percent, about 40 and about 50 percent, less than about 80 percent, less than about 70 percent, less than about 60 percent, or less than about 50 percent.

In other embodiments, a variable porosity stent can include a section not meant for flow diversion having a porosity percentage of between about 80 percent and about 95 percent, about 80 and about 90 percent, or about 90 and about 95 percent.

Similarly, if a stent utilizes a plurality of sections meant for flow diversion, and/or a plurality of sections not meant for flow diversion, the respective ranges of each section utilize the ranges specified above.

One issue with stents is that the stent can normally only be configured and delivered in one direction. This is since a fixed pusher element is connected to one part (e.g., the proximal end) of the stent, and used to navigate the stent out of a packaging unit (typically configured as a dispenser hoop) and into and through a delivery catheter. The pusher mechanism then detaches from the stent through thermolytic, mechanical, or electrolytic means once the stent is expanded within the vasculature. In the context of the embodiments described above involving various configurations of a variable porosity stent (e.g., where only one longitudinal portion of the stent utilizes a low porosity or flow diversion layer), the typical or existing state of the art pusher delivery mechanism would only be connected to one end of the stent. This means the stent can only be delivered such that the low porosity flow diversion portion sits in a fixed manner on either the proximal or distal portion of the stent. In practice, this would mean a manufacturer would need to separately design and sell both: a) stents with a low porosity interface on a proximal region and b) stents with a low porosity interface on a distal region of a stent to cover each scenario.

The following embodiments address this issue by utilizing a packaging and delivery system where a single stent with at least one low porosity and at least one high porosity section can be delivered in either a first, or a second direction. In some embodiments, where a single stent with at least one low porosity and at least one high porosity section are provided, these stents can be delivered in either direction, such that the low porosity section of the stent can either be located on a proximal or distal region of the stent. This can allow the physician to customize the delivery procedure to the patient's needs and can save procedural and manufacturer cost and expense by having a single stent that can be delivered and oriented in either direction to address a particular treatment need (e.g., either a proximally-oriented flow-diversion stent section, or a distally-oriented flow diversion stent section).

Figure 6:
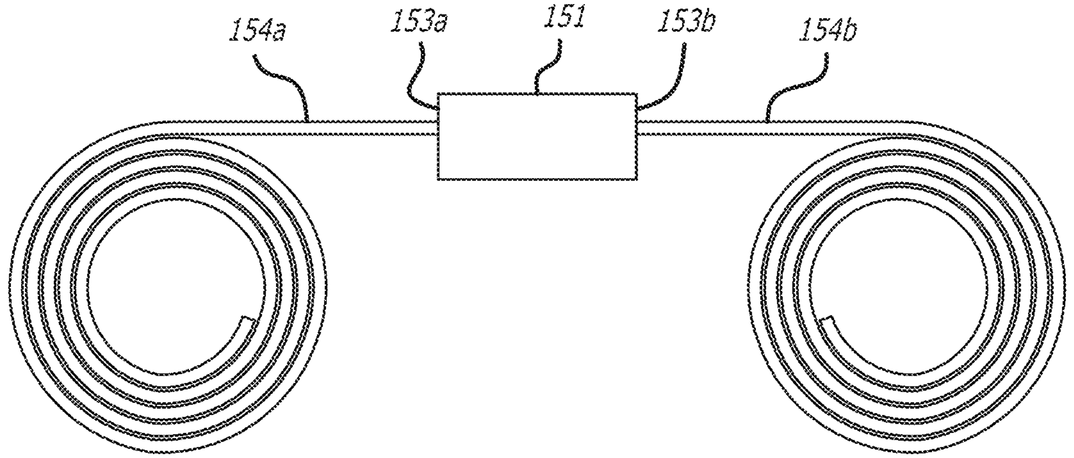
FIG. 6 illustrates a stent packaging and delivery system, according to one embodiment.

FIG. 6 shows an embodiment of a vascular prosthesis packaging and delivery system. In one embodiment, this system reflects how an end user (e.g., physician) receives a vascular prosthesis. The vascular prosthesis device (e.g., stent) is in a housing 151 having a first end 153*a* and a second end 153*b*. First housing section 152*a* can include first tubing 154*a* at first end 153*a* and second housing section 152*b* can include second tubing 154*b* at second end 153*b*. Each of first tubing 154 and second tubing 154*b* can extend into a spiral configuration, with concentric tubing sections—as shown in FIG. 6. Each of first housing 152*a* and second housing 152*b* and its respective connected tubing includes a continuous lumen therein facilitating passage of the stent through first tubing 154*a* or second tubing 154*b*.

In other embodiments, each of first tubing 154 and second tubing 154*b* can be in configurations other than a spiral. In some embodiments, first tubing 154 can be configured in a spiral above or below second tubing 154*b*, thereby saving additional packing space.

Figure 7:
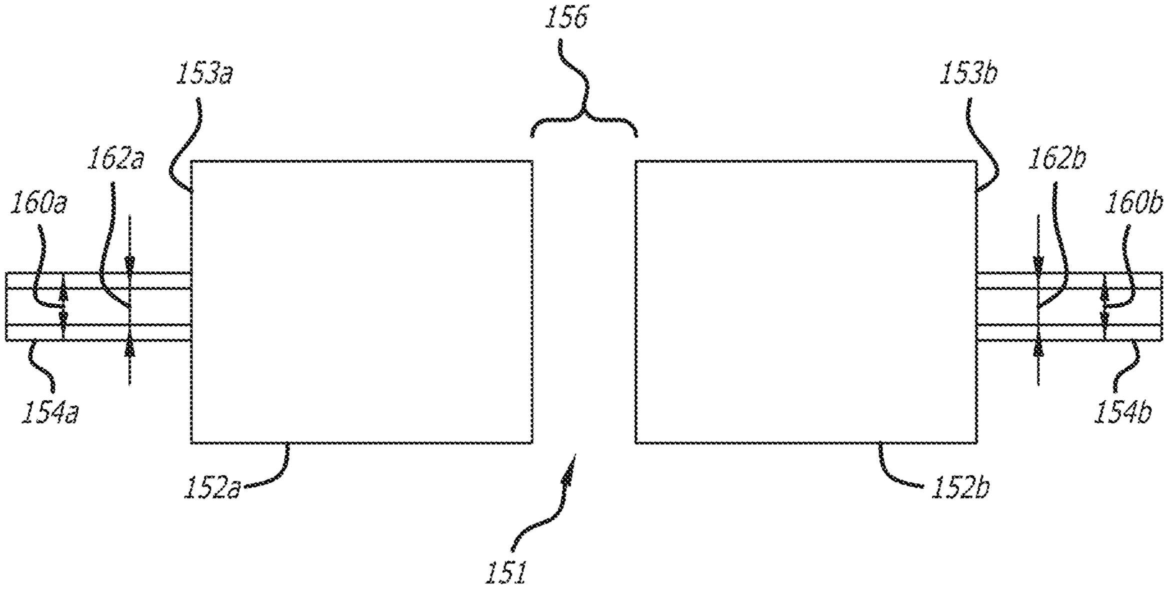
FIG. 7 illustrates a housing used in a stent packaging and delivery system, according to one embodiment.

Housing 151 is shown in more detail in FIG. 7 and includes two housing sections, first housing section 152*a* and second housing section 152*b* separated by gap 156. First tubing section 154*a* extends from first end 153*a* of first housing section 152*a*, and second tubing section 154*b* extends from second end 153*b* of second housing section 152*b*.

As shown in FIGS. 6 and 7, housing 151 (comprised of first housing section 152*a* and second housing section 152*b*) has a larger thickness or outer diameter than the outer diameters 160*a* and 160*b* of first tubing section 154*a* and second tubing section 154*b*.

Further, housing 151 has an internal lumen initially accommodating a stent, this inner lumen has its own associated size or diameter representing the inner passage space. The internal diameter of housing 151 is bigger or larger than the internal diameter 162*a* of first tubing 154*a* and internal diameter 162*b* of second tubing 154*b*.

In one embodiment, first end 153*a* and second end 153*b* of housing 151 (comprising housing sections 152*a* and 152*b*) can include a ramped or funneled shape such that the outer diameter tapers down to outer diameters 160*a* and 160*b* of first tubing 154*a* and second tubing 154*b*—rather than the more abrupt transition shown in FIG. 7.

One embodiment can utilize a housing with a closer diameter, such that the outer diameter of the housing is substantially similar to that of the tubing 154*a*, 154*b*. One embodiment can utilize a housing configuration whereby the internal lumen of first housing section 152*a* and second housing section 152*b* can be substantially similar to that of first tubing 154*a* and second tubing 154*b*.

Stent 150 can be initially contained within both first housing section 152*a* and second housing section 152*b* (see FIG. 8), such that a first portion 161*a* of stent 150 is within first housing section 152*a*, a second portion 161*b* of stent 150 is within second housing section 152*b*, and a medial region 161*c* of stent 150 spans a gap section 156 between first housing section 152*a* and second housing section 152*b*. This initial containment refers to how the stent may be packaged for shipment and how the end user/physician may receive the device/system.

Housing 151 (which is comprised of first housing section 152*a* and second housing section 152*b*) can have an internal cavity or lumen, which is smaller than the fully expanded stent, such that the stent is compressed or constrained when within housing 151. In some embodiments, this internal lumen has a diameter that substantially mirrors the external diameter of the compressed or constrained stent. The stent, as discussed above, is preferably formed of shape memory metallic material so that the stent has a heat-set expanded shape that it takes on when unconstrained.

A mechanical pusher is connected to each end of stent 150, with a first pusher 158*a* connected to a first stent end 165*a* and a second pusher 158*b* connected to a second stent end 165*b*. Each pusher can span the entirety of the relevant coiled tubular section. In this manner, first pusher 158*a* spans the entirety (meaning the entire coiled structure) of tubular portion 154*a* such that it is exposed from the other, open end or terminus of tubular portion 154*a*. Similarly, second pusher 158*b* spans the entirety of tubular portion 154*b* such that it is exposed from the other, open end or terminus of tubular portion 154*b*. Since each pusher extends beyond the terminal end or terminus of each tubular portion, a user can grasp and manipulate each pusher (either 158*a* or 158*b*) to move the stent 150.

Figure 9:
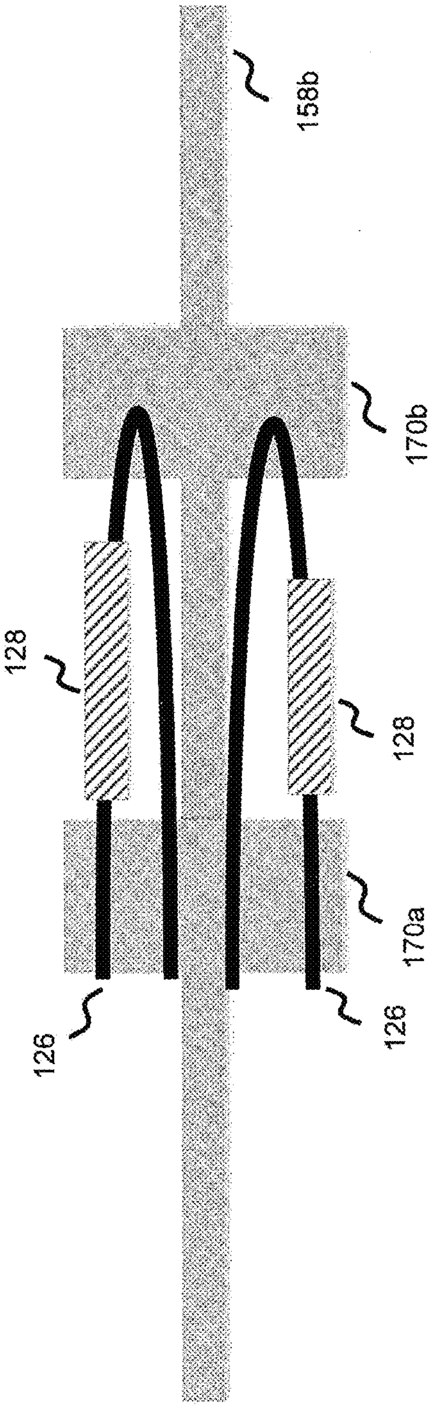
FIG. 9 illustrates a pusher-stent connection interface, according to one embodiment.

The pusher connection to the stent is shown in more detail in FIG. 9—this is shown with respect to pusher 158*b* for illustrative purposes. However, a similar configuration is also used for pusher 158*a*. In one embodiment, pusher 158*b* includes a pair of enlarged bands 170*a*, 170*b*. In one embodiment, bands 170*a*, 170*b* include a radiopaque material such as platinum, palladium, or tantalum to aid in visualization of the connection junction. Flares 126 also utilize marker coils or bands, as discussed above and shown in FIG. 3. The ends of flares 126 are placed within this marker band region, where coils 128 help constrain the stent flares within this region, such that coils 128 are constrained between the enlarged bands 170*a*, 170*b* of pusher 158*b*. In this way, the pusher is mechanically connected to the stent.

The above description discussed how all flares 126 can be of a similar length, or some flares can be larger and some smaller. In one embodiment, only one or some of the plurality of stent flares are gripped between a pusher's enlarged bands 170*a*, 170*b*. In one embodiment, all of the plurality of stent flares are gripped between the pusher's enlarged bands 170*a*, 170*b*. In one embodiment, some stent flares are larger and some smaller, where only the larger stent flares are gripped between the pusher's enlarged bands 170*a*, 170*b*.

In some embodiments, greater than about 5% of stent flares are gripped between a pusher's enlarged bands. In other embodiments, greater than about 10%, greater than about 20%, greater than about 30%, greater than about 40%, greater than about 50%, greater than about 60%, greater than about 70%, greater than about 80%, or greater than about 90% of stent flares are gripped between a pusher's enlarged bands.

In some embodiments, medial region 161*c* of stent 150 is exposed through a gap 156 between first housing section 152*a* and second housing section 152*b*. However, gap 156 is not large enough that the entire stent itself physically expands to its heat set, expansile shape since most of the length of the stent is contained within the smaller diameter housing portions 152*a*, 152*b*. In some embodiments, less than about 5% of medial region of the stent is exposed in gap 156. In other embodiments, less than about 10%, less than about 20%, less than about 30%, less than about 40%, or less than about 50% of medial region of the stent is exposed in gap 156.

Figure 8:
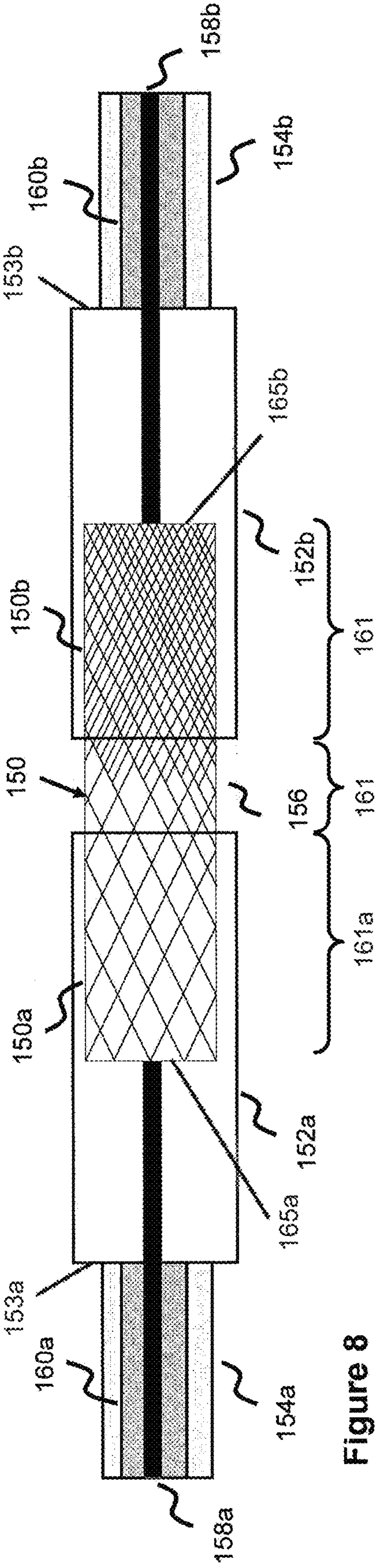
FIG. 8 illustrates a close-up view of a stent packaging and delivery system, according to one embodiment.

To propel the stent through first tubing 154*a*, the user simply pulls pusher 158*a* (e.g., towards the left direction, in the context of FIG. 8). Pusher 158*a* is connected to first stent end 165*a*. As the stent is first pulled toward first tubing 154*a* (e.g., left in the context of FIG. 8), the second stent end 165*b* passes through gap 156 into housing portion 152*a*. When the terminal end (in the context of FIG. 8, the right terminal end, second stent end 165*b*) of the stent passes through gap 156, the stent is slightly exposed and allowed to expand slightly—meaning the flares start to protrude out from second housing 152*b*. Once this occurs, pusher 158*b* disengages from second stent end 165*b* as the stent flares are no longer constrained within enlarged bands 170*a*, 170*b* of pusher 158*b*. At this point, the stent is solely connected to pusher 158*a* and is navigated through first housing portion 152*a* and connected first tubing 154*a* by moving the pusher (in this case, by pulling pusher 158*a* leftwards, in the context of FIG. 8).

Gap 156 as described above is simply configured to allow the stent ends to expand as the respective end passes there through, thereby disengaging the opposing pusher. In one embodiment, this gap is complete such that there is a circumferential space or void formed between first housing section 152*a* and second housing section 152*b* which forms gap 156. In another embodiment, there is one or more small slits of material connecting first housing section 152*a* and second housing section 152*b* such that there is still a majority gap section defined, but also a small connection point between first housing section 152*a* and second housing section 152*b*. Since most of the space between first housing section 152*a* and second housing section 152*b* is still defined by open space or a "gap", the stent end can still expand to some degree as the stent passes through, thereby disengaging the other opposing pusher.

To pass the stent through second tubing 154*b*, the user simply engages pusher 158*b* (in the context of FIG. 8, pulling the pusher 158*b* toward the rightward direction). Doing so will cause the first stent end 165*a* (in the context of FIG. 8) to pass through gap 156, thereby allowing the stent flares to extent and disengaging the stent from pusher 158*a*.

Figure 10:
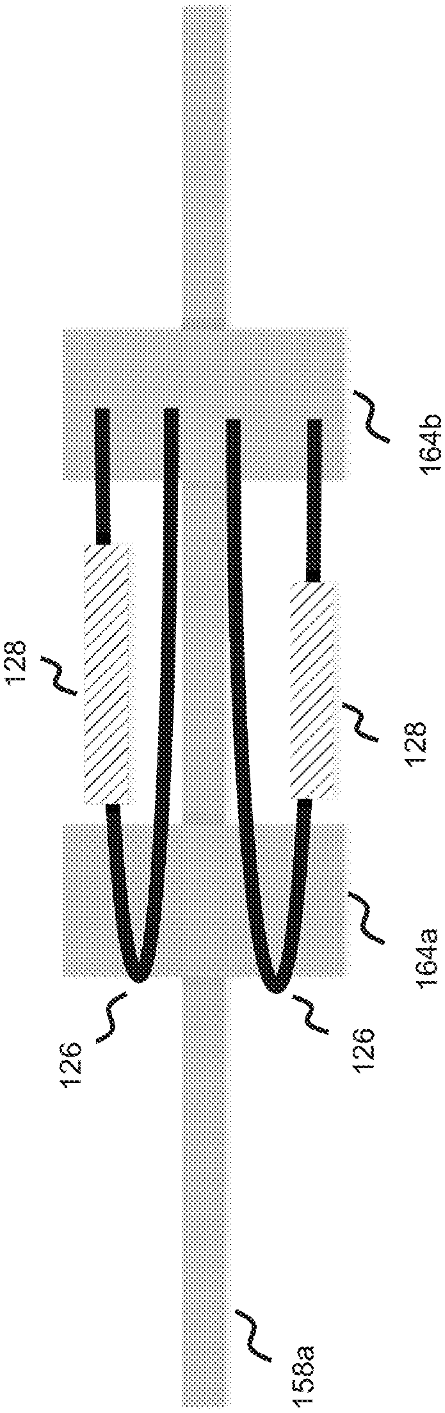
FIG. 10 illustrates a pusher-stent connection interface, according to one embodiment.

The configuration of stent 150's connection to pusher 158*a* is shown in FIG. 10 and is basically the same as FIG. 9 except the opposite end of the stent/stent flares are engaged. Like the above description, pulling pusher 158*b* (toward the right, in the context of FIG. 8) will cause pusher 158*a* to disengage from the opposing side of the stent as stent 150 passes through gap 156.

Each of first tubing 154*a* and second tubing 154*b* includes a smaller introducer tube or sleeve along a section of the tubing portion—as shown in FIG. 8. First tubing 154*a* includes a first introducer tube/sleeve 164*a*, and second tubing 154*b* includes a second introducer tube/sleeve 164*b*. When stent 150 is pulled into first tubing 154*a* or second tubing 154*b*, it is actually pulled into either first introducer tube/sleeve 164*a* or second introducer tube/sleeve 164*b* which sits within first tubing 154*a* or second tubing 154*b*. The introducer tube in regard to the coiled tubular portion is shown in more detail in FIGS. 11A-11B, where first tubing 154*a* includes first introducer tube/sleeve 164*a* within a portion of the tubing, and second tubing 154*b* includes second introducer tube/sleeve 164*b* within a portion of the tubing. When a user manipulates the pusher, for example in the context of FIG. 8 pulling pusher 158*a* leftwards into first introducer tube/sleeve 164*a* which resides in first tubing 154*a*, the stent enters into the introducer tube until it is fully contained within the introducer tube. Continued manipulation of pusher 158*a* can pull the stent through the remainder of first tubing 154*a* once it is contained in first introducer tube/sleeve 164*a*.

Likewise, when a user manipulates the pusher, for example in the context of FIG. 8 pulling pusher 158*b* rightwards into second introducer tube/sleeve 164*b* which resides in second tubing 154*b*, the stent enters into the introducer tube until it is fully contained within the introducer tube. Continued manipulation of pusher 158*b* pulls the stent through the remainder of second tubing 154*b* once it is contained in second introducer tube/sleeve 164*b*.

In other embodiments, the ends of a stent (including the looped or flared regions) can be preloaded into first introducer tube/sleeve 164*a* and second introducer tube/sleeve 164*b*. In one embodiment, in order to better facilitate entry of a stent into the introducer tube, each end of stent 150 is preloaded, respectively, into first introducer tube/sleeve 164*a* and second introducer tube/sleeve 164*b*. In this way, one end of stent 150 is located within first introducer tube/sleeve 164*a* (first introducer tube/sleeve 164*a* being located within first tubing 154*a*), and the other end of stent 150 is located within second introducer tube/sleeve 164*b* (second introducer tube/sleeve 164*b* being located within second tubing 154*b*). This configuration can have further advantages, for example, allowing housing 151 (including first housing section 152*a* and second housing section 152*b*) to be sized larger since pusher 158*a*, 158*b* connects to the collapsed stent ends, which are housed, respectively, in first introducer tube/sleeve 164*a* and second introducer tube/sleeve 164*b*.

In another embodiment utilizing the pre-loaded stent-end approach outlined above, first introducer tube/sleeve 164*a* and second introducer tube/sleeve 164*b* sit beyond the ends of first tubing 154*a* and second tubing 154*b* such that they reside within a lumen of both first housing section 152*a* and second housing section 152*b*. This can allow the ends of the stent to be preloaded into first introducer tube/sleeve 164*a* and second introducer tube/sleeve 164*b* while still allowing the stent to initially physically reside entirely within both first housing section 152*a* and second housing section 152*b*—thereby making it easier for the stent to enter into respective introducer tube (e.g., first introducer tube/sleeve 164*a* or second introducer tube/sleeve 164*b*).

In one embodiment, first tubing 154*a* and second tubing 154*b*, which overlie first introducer tube/sleeve 164*a* and second introducer tube/sleeve 164*b*, can utilize a mechanical fitting to help ensure that the introducer is selectively fixed in place while the entirety of stent 150 is being loaded into the respective introducer. For example, a portion of first tubing 154*a* and/or second tubing 154*b* near first end 153*a* and/or second end 153*b* of housing 151 can utilize a slot or cut-out region, where first introducer tube/sleeve 164*a* and/or second introducer tube/sleeve 164*b* utilize a corresponding slot or cut-out region. The user can engage a pin that passes through the cut-out regions to engage first introducer tube/sleeve 164*a* and/or second introducer tube/sleeve 164*b*, thereby fixing the introducer in place as the stent is being placed into the introducer. Once stent 150 is properly loaded into first introducer tube/sleeve 164*a* and second introducer tube/sleeve 164*b*, the user can then remove the pin to disengage the introducer allowing it to then translate through the overlying first tubing 154*a* or second tubing 154*b*.

The fitting interface can be tweaked based on the stent packaging configuration. For instance, if first introducer tube/sleeve 164*a* and second introducer tube/sleeve 164*b* are partially loaded in first housing section 152*a* and second housing section 152*b* (as described in one embodiment above) such that each end of stent 150 is pre-loaded into first introducer tube/sleeve 164*a* and second introducer tube/sleeve 164*b*, then the fitting can be placed on the housing such that the pin would overlie the housing and the underlying end of a corresponding introducer sleeve. In this manner, the introducer sleeve is engaged and prevented from moving as the stent enters into the respective introducer sleeve.

In one embodiment, each respective fitting is positioned near first and second housing sections 152*a*, 152*b* such that the fitting is near the position of stent 150 as the stent enters into the respective introducer sleeve 164*a* or 164*b*. However, the slot or cut-out of tubing 154*a*/154*b* and underlying introducer sleeve 164*a*, 164*b* do not extend all the way through tubing 154*a*/154*b* and introducer sleeve 164*a*/164*b* (and thus are only along one side of each). In this way, the pin will not necessarily contact stent 150 as it enters the respective introducer sleeve 164*a* or 164*b*. In another embodiment, the fittings are positioned further along the tubing 154*a*/154*b*, such that the stent will not enter into the relevant section of the underlying introducer sleeve 164*a*/164*b* upon entry into the tubing. In this embodiment, the slot or cut-out region can have a configuration whereby it passes all the way through the tubing and underlying introducer sleeve, and will not interfere with passage of the stent. Once stent 150 has entered the respective introducer sleeve 164*a* or 164*b*, the pin is disengaged or removed to allow the introducer sleeve 164*a*/164*b* to pass through overlying tubing 154*a*/154*b*.

Each of first introducer tube/sleeve 164*a* or second introducer tube/sleeve 164*b* is preferably closely dimensioned to the respective first tubing 154*a* or second tubing 154*b* which the introducer tube resides within to ease passage of stent 150 into the introducer tube as the user engages the proper pusher element 158*a* or 158*b*. As such, in some embodiments, it is preferable that the outer diameter of first introducer tube/sleeve 164*a* and/or second introducer tube/sleeve 164*b* is closely matched to the inner diameter of first tubing 154*a* and/or second tubing 154*b*.

As described above, as the user engages the respective pusher (e.g., pusher 158*a*), stent 150 can exit housing 151 and enter the introducer tube residing within the respective tubing (e.g., first introducer tube/sleeve 164*a* in first tubing 154*a*). First introducer tube/sleeve 164*a*, as shown in FIG. 11, only spans part of first tubing 154*a*. Though first introducer tube/sleeve 164*a* is not illustratively shown as spanning into the coiled part of first tubing 154*a*, it can be sized shorter or longer as needed, for instance sized at a length that would extend into the coiled section. However, first introducer tube/sleeve 164*a* is shorter than first tubing 154*a*, such that it does not extend along the entirety of the tubing.

The introducer tube/sleeve is dimensioned longer than the stent and is meant to house the stent as the stent passes through the entirety of first tubing 154*a* or second tubing 154*b*. Once the stent is completely within the introducer tube, further translation of the pusher will translate the introducer tube (e.g., first introducer tube/sleeve 164*a*) through the respective tubing (e.g., first tubing 154*a*) until the introducer tube exits the tubular portion. Once first introducer tube/sleeve 164*a* or second introducer tube/sleeve 164*b* exits the tubing or tubular housing, the introducer tube is introduced into a catheter (either through a catheter hub, or a hemostatic valve of a catheter). The introducer is sized slightly larger than the catheter, so as the user engages the pusher by pushing the pusher distally with respect to the static catheter, the stent passes through the larger introducer tube lumen and into the smaller catheter lumen.

The earlier description noted the nature of the variable porosity stent, in that at least one section has a lower porosity and at least one section has a higher porosity. This is shown with respect to the housing and delivery system in FIG. 8, where stent 150 includes high porosity region 150*a* and low porosity region 150*b*. The earlier description further noted that the stent housing and delivery system can allow the stent to be customized such that low porosity region or flow-diversion region 150*b* can either be on a proximal or distal portion of the stent. This will now be explained in more detail, with respect to the housing and delivery system.

Figure 11A:
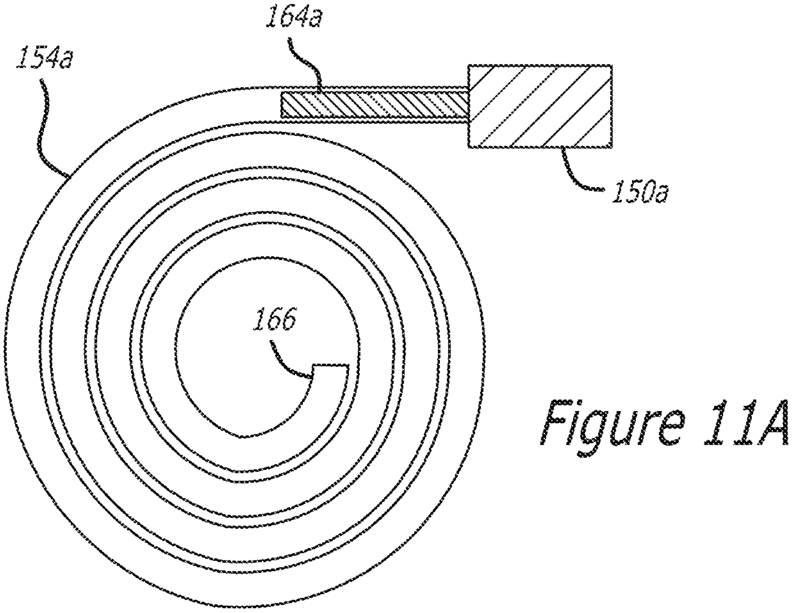
FIG. 11A illustrates a tubing portion used in a stent packaging and delivery system, according to one embodiment.
Figure 12:
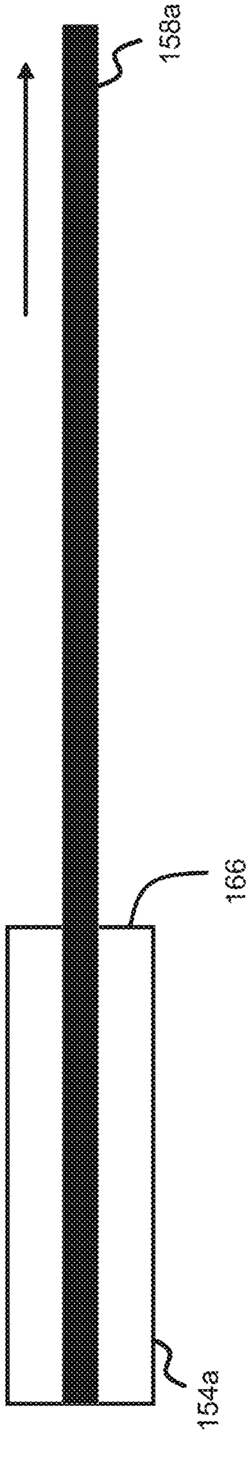
FIG. 12 illustrates an exit port of the tubing portion of FIG. 11A.
Figure 13:
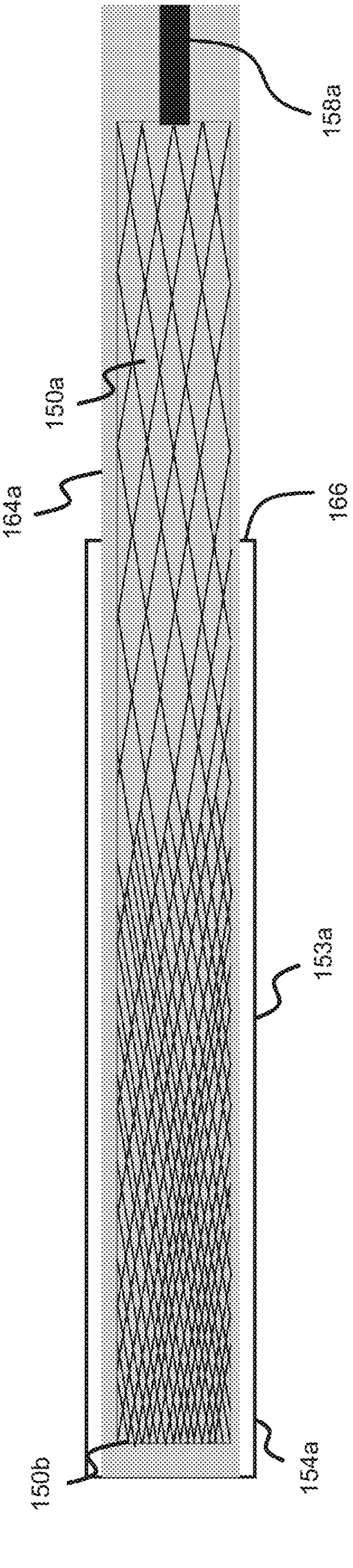
FIG. 13 illustrates a stent passing through the exit port of FIG. 12.

If stent 150 is pulled in one direction (e.g., towards the left in the context of FIG. 8), the high porosity region 150*a* is the first section to enter introducer tube 164*a* (which resides in coiled first tubing 154*a*) and low porosity section 150*b* will be the last section to enter the introducer tube. As shown in FIG. 11A, end 166 of coiled first tubing 154*a* (in the interior of the coiled first tubing 154*a*) has an opening as shown in FIG. 12 which pusher 158*a* passes through, and in this way the user can manipulate the connected stent (e.g., stent 150) into first introducer tube/sleeve 164*a*. As can be appreciated in the context of FIGS. 8, 11A and 11B, since the high porosity portion 150*a* is the first portion of the stent to enter first introducer tube/sleeve 164*a*, it is also the first section of the stent to exit from first end 153*a* of overlying tubular portion 154*a*—as shown in FIG. 13. Since first introducer tube/sleeve 164*a* is generally oversized compared to stent 150, the last part of stent 150 to be introduced into first introducer tube/sleeve 164*a* (low porosity portion 150*b*, in the context of FIG. 13) will be generally flush with one end of first introducer tube/sleeve 164*a* while there may be a gap between the other end of the stent (high porosity portion 150*a*, in the context of FIG. 13) and the corresponding end of first introducer tube/sleeve 164*a*. When first introducer tube/sleeve 164*a* is completely removed from first tubing 154*a*, low porosity section 150*b* will be at one end of first introducer tube/sleeve 164*a*.

Figure 14:
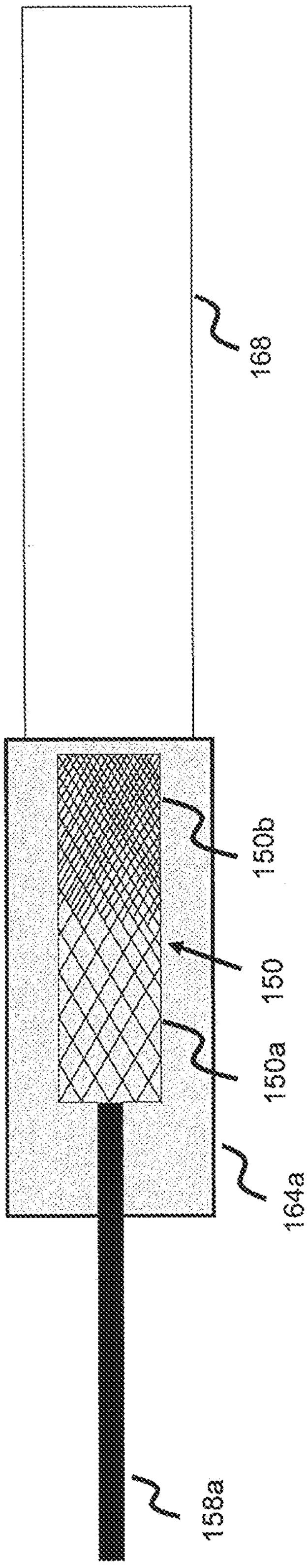
FIG. 14 illustrates a stent with a distally-oriented flow diversion portion being introduced into a catheter, according to one embodiment.

To place the stent into the catheter, the configuration is simply flipped from how first introducer tube/sleeve 164*a* is withdrawn from first tubing 154*a*. The user places the other end of the introducer tube (the portion farther from the pusher 158*a*) into the catheter hub or catheter hemostasis valve—as shown in FIG. 14. Logically, this makes sense since the only way the user can deliver the stent is by being able to grip the pusher to maneuver the stent. In the context of FIG. 14, first introducer tube/sleeve 164*a* can be thought of as already placed within a catheter hub or hemostasis valve, where the stent is now ready to be introduced into catheter tubing 168 while first introducer tube/sleeve 164*a* (having a larger diameter) remains in the catheter hub or hemostasis valve where it is withdrawn once stent 150 is delivered into the catheter tubing. The user pushes pusher 158*a* distally to move stent 150 from the introducer sleeve into catheter tubing 168. The first introducer tube/sleeve 164*a* has a diameter that is larger than the diameter of the catheter tubing. Therefore, engaging the pusher can navigate stent 150 into catheter tubing 168, while first introducer tube/sleeve 164*a* remains. In this configuration, as is shown in FIG. 14, low porosity region 150*b* of the stent is located on the distal portion of the stent since this was the manner it was delivered from housing 151 (see FIGS. 8 and 13), and high porosity region 150*a* of the stent is located on the proximal portion of the stent.

Please note with reference to the above, the term distal is used in regard to the direction of the patient vasculature, while proximal refers to the direction outside of the patient's body where access to the vasculature occurs. In this manner, the user will push the pusher distally to move the stent into the vasculature, and the low porosity portion 150*b* is distally positioned while the high porosity portion 150*a* is proximally positioned.

Figure 11B:
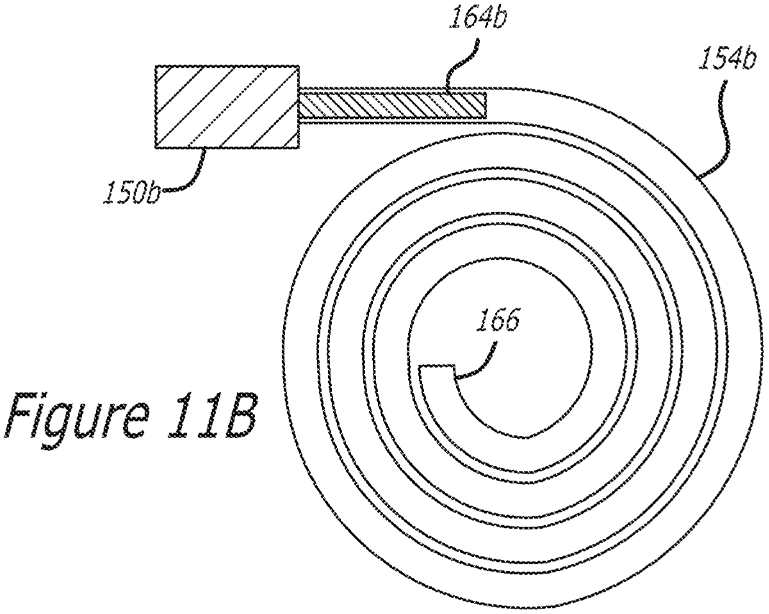
FIG. 11B illustrates another tubing portion used in a stent packaging and delivery system, according to one embodiment.
Figure 15:
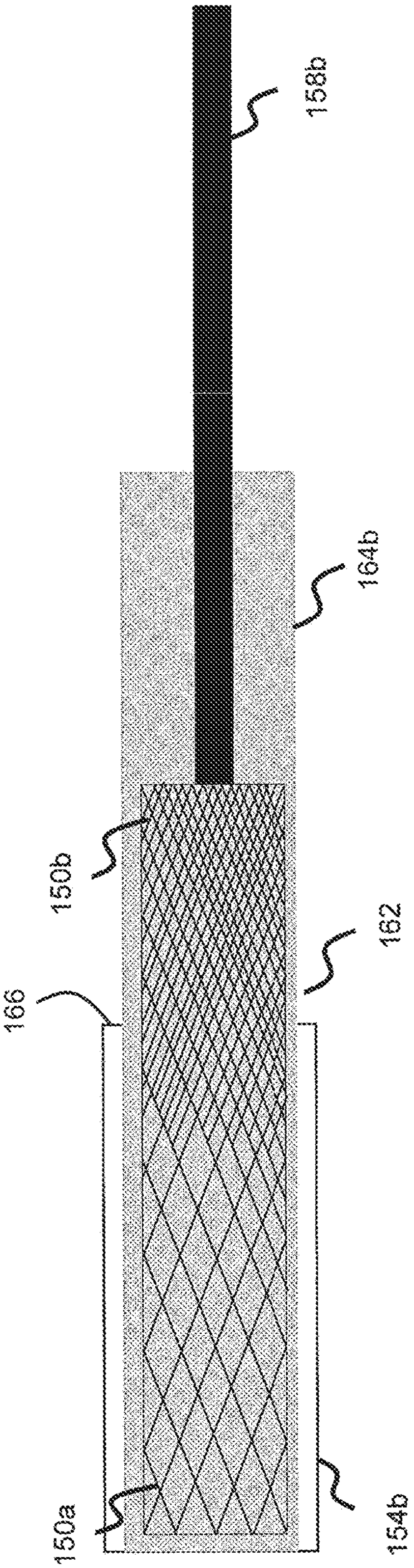
FIG. 15 illustrates a stent passing through an exit port of a tubing portion of a stent packaging and delivery system, according to one embodiment.
Figure 16:
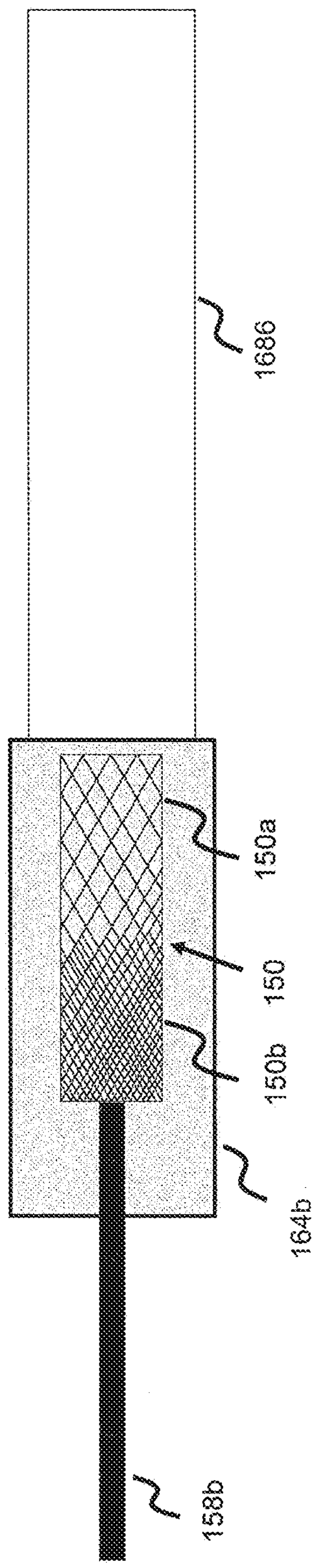
FIG. 16 illustrates a stent with a proximally-oriented flow diversion portion being introduced into a catheter, according to one embodiment.

If the user desires that low porosity region 150*b* of the stent be seated proximally (e.g., in a scenario where a branched artery sits distally near an aneurysm, such that it would be desirable to have a proximal low-porosity section and a distal high-porosity section), the user would simply reverse the configuration (see FIG. 8) by engaging pusher 158*b* instead of pusher 158*a* to pull the stent into second introducer tube/sleeve 164*b* which resides in second tubing 154*b* (e.g., see FIG. 11B). When the stent is engaged in this format, the stent will emerge from end 166 of second tubing 154*b* in the configuration shown in FIG. 15, where low porosity region 150*b* comes out first and high porosity region 150*a* comes out last. The user can then orient the introducer tube 164*b* in the manner shown in FIG. 16, whereby high porosity region 150*a* is oriented toward the distal section of second introducer tube/sleeve 164*b* and low porosity region 150*b* is oriented toward the proximal section of second introducer tube/sleeve 164*b*.

Further variations are possible. For instance, FIG. 8 illustratively shows high porosity region 150*a* of the stent being adjacent first tubing 154*a*/first introducer tube/sleeve 164*a*. However, this can be flipped such that high porosity region 150*a* instead is adjacent the opposite second tubing 154*b*/second introducer tube/sleeve 164*b*. The delivery configuration to orient the stent such that the low porosity flow diverter region sits on a particular preferred section of the stent, would then be flipped.

Other embodiments can vary the location of first housing sections 152*a* and second housing section 152*b*. In the context of FIG. 6, the housing section is shown as being located outside the periphery of the concentric spirals forming first tubing 154*a* and second tubing 154*b*—and where exit port or end 166 are each located along the most-inward concentric spiral (as shown in FIG. 11). This can be varied in other embodiments, such that the housing is directly connected to the most inward spiral forming first tubing 154*a* and second tubing 154*b* while end 166 is along the most outward concentric spiral. Other embodiments can disregard the spiral dispenser housing shapes in favor of other shapes (e.g., linear, rectangular, or other shapes).

Further, though the housing and delivery description specifically mentioned how the delivery configuration would work with a stent utilizing only two porosity sections, the other stent embodiments contemplated earlier discussed three or more porosity sections with various combinations of low porosity and high porosity sections.

Though the term stent is often used in the specification, the embodiments described herein can be used on a variety of vascular-prosthesis devices, such as stents, stent-grafts, and vascular scaffolds.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A vascular prosthesis system comprising:

a vascular prosthesis having a lower porosity region and a higher porosity region;

a housing containing the vascular prosthesis;

a first tubing linked to a first end of the housing, a second tubing linked to a second end of the housing; and a first pusher connected to a first section of the vascular prosthesis, and a second pusher connected to a second section of the vascular prosthesis, the vascular prosthesis being deliverable through the first tubing or the second tubing.

2. The vascular prosthesis system of claim 1, wherein the first tubing and the second tubing each contain an introducer sleeve.

3. The vascular prosthesis system of claim 2, wherein terminal ends of the vascular prosthesis are pre-loaded into each introducer sleeve.

4. The vascular prosthesis system of claim 2, wherein at least one of the introducer sleeves spans a portion of the housing.

5. The vascular prosthesis system of claim 2, further comprising a pin which engages at least one of the introducer sleeves.

6. The vascular prosthesis system of claim 1, wherein the first tubing and the second tubing are both coiled.

7. The vascular prosthesis system of claim 1, wherein delivery through the first tubing causes the lower porosity region to be on a proximal region of the vascular prosthesis, and delivery through the second tubing causes the lower porosity region to be on a distal region of the vascular prosthesis.

8. A vascular prosthesis system comprising:

a vascular prosthesis having a first porosity region and a second porosity region;

a housing containing the vascular prosthesis;

a first tubing linked to a first end of the housing, a second tubing linked to a second end of the housing; and a first pusher connected to a first section of the vascular prosthesis, and a second pusher connected to a second section of the vascular prosthesis, wherein the vascular prosthesis being deliverable through the first tubing or the second tubing; and wherein if the vascular prosthesis is delivered through the first tubing, then the first porosity region is on a first longitudinal section of the vascular prosthesis; and if the vascular prosthesis is delivered through the second tubing, then the first porosity is on a second longitudinal section of the vascular prosthesis.

9. The vascular prosthesis system of claim 8, wherein the first pusher is used to navigate the vascular prosthesis through the first tubing and the second pusher is used to navigate the vascular prosthesis through the second tubing.

10. The vascular prosthesis system of claim 8, wherein the first pusher can disengage from the first section of the vascular prosthesis.

11. The vascular prosthesis system of claim 8, wherein the second pusher can disengage from the second section of the vascular prosthesis.

12. The vascular prosthesis system of claim 8, wherein the first pusher disengages from the vascular prosthesis as the vascular prosthesis is delivered through the second tubing.

13. The vascular prosthesis system of claim 8, wherein the second pusher disengages from the vascular prosthesis as the vascular prosthesis is delivered through the first tubing.

14. The vascular prosthesis of claim 8, wherein the vascular prosthesis includes flared ends and wherein the first pusher and the second pusher engage the flared ends of the vascular prosthesis.

15. A flow diverting prosthesis system comprising:

a vascular prosthesis having a flow diversion region with a lower porosity and a non-flow diversion region with a higher porosity;

a housing containing the vascular prosthesis;

a first tubing linked to a first end of the housing, a second tubing linked to a second end of the housing; and a first pusher connected to a first section of the vascular prosthesis, and a second pusher connected to a second section of the vascular prosthesis, wherein the vascular prosthesis being deliverable through the first tubing or the second tubing; and wherein if the vascular prosthesis is delivered through the first tubing, then the flow diversion region is on a first longitudinal section of the vascular prosthesis; and if the vascular prosthesis is delivered through the second tubing, then the flow diversion region is on a second longitudinal section of the vascular prosthesis.

16. The vascular prosthesis system of claim 15, wherein the housing has a first housing section, a second housing section, and a gap in between the first housing section and the second housing section.

17. The vascular prosthesis system of claim 15, wherein a lumen of the housing is larger than a lumen of the first tubing and a lumen of the second tubing.

18. The vascular prosthesis system of claim 15, wherein an outer diameter of the housing is larger than an outer diameter of the first tubing and an outer diameter of the second tubing.

19. The vascular prosthesis system of claim 15, wherein delivery through the first tubing causes the flow diversion region to be on a proximal region of the vascular prosthesis, and delivery through the second tubing causes the flow diversion region to be on a distal region of the vascular prosthesis.

20. A vascular prosthesis system comprising:

a vascular prosthesis having a lower porosity region and a higher porosity region;

a housing containing the vascular prosthesis; and a first tubing linked to a first end of the housing, a second tubing linked to a second end of the housing, wherein the first tubing and the second tubing are both coiled, the vascular prosthesis being deliverable through the first tubing or the second tubing.

* * * * *